(12) United States Patent
Hay (10) Patent No.: US 10,288,540 B1
(45) Date of Patent: May 14, 2019

(54) INSTRUMENTED INDENTATION APPARATUS HAVING INDENTER PUNCH WITH FLAT END SURFACE AND INSTRUMENTED INDENTATION METHOD USING THE SAME

(71) Applicant: KLA-Tencor Corporation, Milpitas, CA (US)

(72) Inventor: Jennifer Hay, Knoxville, TN (US)

(73) Assignee: KLA-Tencor Corporation, Milpitas, CA (US)

( * ) Notice: Subject to any disclaimer, the term of this patent is extended or adjusted under 35 U.S.C. 154(b) by 68 days.

(21) Appl. No.: 14/556,035

(22) Filed: Nov. 28, 2014

(51) Int. Cl.
    *G01N 3/48* (2006.01)
    *G01N 3/42* (2006.01)
    *G01N 3/40* (2006.01)

(52) U.S. Cl.
    CPC ............. *G01N 3/48* (2013.01); *G01N 3/40* (2013.01); *G01N 3/42* (2013.01)

(58) Field of Classification Search
    CPC .. G01N 3/42; G01N 3/40; G01N 3/48; G01N 2203/0286; G01N 2203/0082; G01N 2203/0078
    USPC .............................. 73/82, 81, 78, 83, 12.01
    See application file for complete search history.

(56) References Cited

U.S. PATENT DOCUMENTS

| | | | | |
|---|---|---|---|---|
| 3,738,161 A | * | 6/1973 | Lucke, Jr. ............... | G01N 3/44 73/85 |
| 4,848,141 A | * | 7/1989 | Oliver .................... | G01N 3/405 73/81 |
| 4,852,397 A | * | 8/1989 | Haggag ................... | G01N 3/42 73/82 |
| H1456 H | * | 7/1995 | Jero ........................ | 73/661 |
| 5,490,416 A | * | 2/1996 | Adler ...................... | G01N 3/42 73/82 |
| 5,999,887 A | * | 12/1999 | Giannakopoulos ...... | G01N 3/42 702/33 |
| 6,053,034 A | * | 4/2000 | Tsui ........................ | G01N 3/42 73/81 |
| 6,247,355 B1 | * | 6/2001 | Suresh .................... | G01N 3/42 73/82 |
| 7,441,465 B2 | | 10/2008 | Oliver et al. | |
| 8,631,687 B2 | | 1/2014 | Patten et al. | |
| 2003/0060987 A1 | * | 3/2003 | Dao ........................ | G01N 3/42 702/42 |
| 2003/0222871 A1 | * | 12/2003 | Brombolich ........... | G06F 17/5018 345/427 |

(Continued)

OTHER PUBLICATIONS

Hans-Jakob Schindler, On quasi-non-destructive strength and toughness testing of elastic-plastic materials, International Journal of Solids and Structures 42 (2005) 715-725.*

(Continued)

*Primary Examiner* — Son T Le
*Assistant Examiner* — Marrit Eyassu
(74) *Attorney, Agent, or Firm* — Hodgson Russ LLP (57) ABSTRACT

An instrumented indentation apparatus and instrumented indentation method, for use in instrumented indentation, employ a flat-ended indenter (punch). Force-displacement data of a loading operation, in which a sample is indented using the indenter, and the known value of the effective radius of the end surface of the indenter, are used to calculate values of stress and strain. The entire stress-strain curve for the sample may be produced from these values.

12 Claims, 8 Drawing Sheets

(56) References Cited

U.S. PATENT DOCUMENTS

| | | | | |
|---|---|---|---|---|
| 2004/0011119 A1* | 1/2004 | Jardret | ............ | G01N 3/46 |
| | | | | 73/81 |
| 2004/0020276 A1* | 2/2004 | Kwon | ............ | G01N 3/48 |
| | | | | 73/81 |
| 2009/0076743 A1* | 3/2009 | Moseson | ............ | G01N 3/42 |
| | | | | 702/42 |
| 2010/0281963 A1* | 11/2010 | Greer | ............ | G01N 3/08 |
| | | | | 73/82 |
| 2012/0022802 A1* | 1/2012 | Sakuma | ............ | G01N 3/42 |
| | | | | 702/43 |
| 2014/0090480 A1* | 4/2014 | Adams | ............ | G01N 3/42 |
| | | | | 73/818 |

OTHER PUBLICATIONS

Hay, "Introduction to Instrumented Indentation Testing", Experimental Techniques, 33(6): p. 66-72, Nov./Dec. 2009.

Johnson, "Normal Contact of Inelastic Solids", Contact Mechanics,1987, Cambridge University Press, New York, p. 153-201.

Tabor, The Hardness of Metals, 1951, London, Oxford University Press, p. 72-75.

Herbert, et al., "On the Measurement of Stress-Strain Curves by Spherical Indentation", Thin Solid Films, 2001, 398: p. 331-335.

Hay, et al., "Measuring the Complex Modulus of Polymers by Instrumented Indentation Testing", Experimental Techniques, 2011.

Uchic, et al., "Sample Dimensions Influence Strength and Crystal Plasticity", Science, 2004, 305(5686), p. 986-989.

Hay, et al. "Continuous Stiffness Measurement during Instrumented Indentation Testing", Experimental Techniques, 2010. 34(3): p. 86-94.

Pharr, et al., "On the Generality of the Relationship among Contact Stiffness, Contact Area, and Elastic-Modulus during Indentation", Journal of Materials Research,1992. 7(3): p. 613-617.

Doerner, et al., "A Method for Interpreting the Data from Depth-Sensing Indentation Instruments", Journal of Materials Research, 1986. 1(4): p. 601-609.

Cheng, et al., "Scaling, Dimensional Analysis, and Indentation Measurements", Materials Science and Engineering R, 2004, 44: p. 91-149.

Hay, et al. "Using the Ratio of Loading Slope and Elastic Stiffness to Predict Pile-Up and Constraint Factor During Indentation", Symposium T—Fundamentals of Nanoindentation & Nanotribology, 1998, Boston, MA: Materials Research Society, p. 101-106.

Lu, et al. "Finite element analysis of cylindrical indentation for determining plastic properties of materials in small volumes", J. Phys. D: Appl. Phys. 41 (2008).

Shilkrot, et al. "Multiscale plasticity modeling: coupled atomistics and discrete dislocation mechanics", Journal of the Mechanics and Physics of Solids 52 (2004) 755-787.

ISO/FDIS, "Metallic materials—Instrumented indentation test for hardness and materials parameters—Part 1: Test method", 2002.

Li, et al. "Testing the Limits of Indentation", Research and Development, Nov. 25, 2014.

Bei, et al. "Compressive strengths of molybdenum alloy micropillars prepared using a new technique", Scripta Materialia, 2007.

* cited by examiner

FIG.8

INSTRUMENTED INDENTATION APPARATUS HAVING INDENTER PUNCH WITH FLAT END SURFACE AND INSTRUMENTED INDENTATION METHOD USING THE SAME

BACKGROUND

Figure 1:
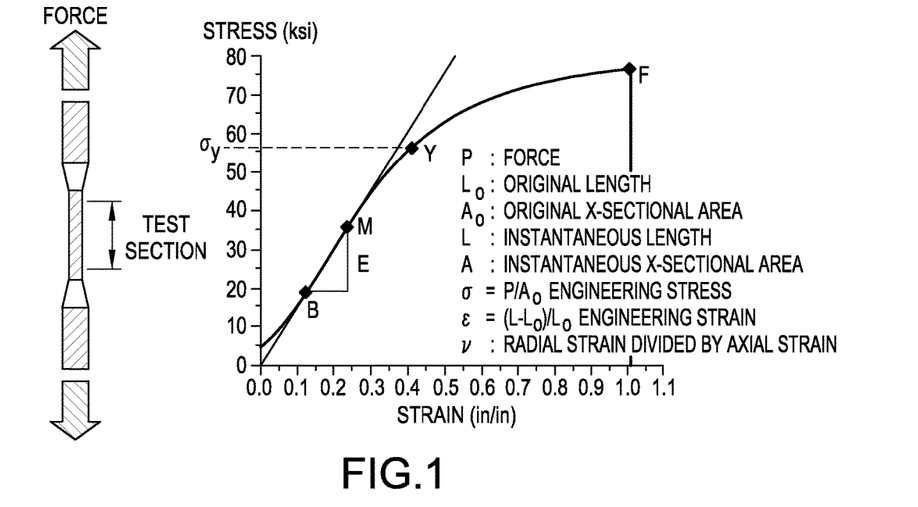
FIG. 1 is a diagram of a macro-scale mechanical tensile test of a sample and includes a schematic representation of a sample being tested and a stress-strain curve constructed from data produced by the tensile test.

The simplest and most common macro-scale mechanical test is the tensile (or compression) test. In this test, a sample of uniform cross section is stretched (or compressed) uniaxially while the resulting deformation of the sample is continuously monitored. The stress a is defined as the force applied to the sample divided by the cross-sectional area of the sample, and the strain E is defined as the change in length of the sample divided by the original length. A typical plot from such a test is shown in FIG. 1.

The strain increases in proportion to the stress while the deformation remains elastic, with the constant of proportionality being the Young's Modulus of the material, E. The onset of plasticity is identified as the yield point, or the point at which the strain begins to increase disproportionately to the stress. The yield point is designated "Y" in FIG. 1. Beyond the yield point Y, a variety of micro-structural mechanisms determine the relation between stress and strain; these include dislocation motion and entanglement, grain boundary sliding, micro-fracturing, etc.

Due to the prevalence of the tensile test, many mechanical computational models require, as input, the stress-strain curve of the material.

However, the design and manufacturing of products on a small scale, e.g., where dimensions may be on the order of microns, cannot be accomplished using properties of materials measured with macro-sized samples because the properties of a material depends on its micro-structure, which in turn depends on the scale of the material. Accordingly, instrumented indentation has emerged as the premier method for measuring mechanical properties of small scale samples (i.e., small volumes of materials).

Standardized instrumented indentation can be used to determine the Young's modulus as well as the hardness of a small volume of material.

One class of indentation equipment or "nanoindenters" for carrying out instrumented indentation commonly employs a geometrically self-similar indenter punch, e.g., a self-similar pyramidal indenter punch known as a Berkovich indenter tip. A Berkovich indenter tip, however, can impose only one effective strain on the test material. Thus, a Berkovich indenter tip cannot be used to determine the relationship between stress and strain beyond the yield point.

Nanoindenters having a spherical type of indenter have been used to derive the mechanical stress-strain curve with limited success. With these indenters, a spherical surface of an indenter punch is forced into the test material, and the strain imposed on the test material increases with the indentation force. When the spherical surface of the indenter punch first contacts the surface of the test material, the strain is small, and the deformation is elastic. The imposed strain increases as the indenter punch is pressed further into the test material, and eventually causes plastic yield in the test material. David Tabor demonstrated, circa 1956, that the hardness measured with a spherical indenter could be scaled so as to overlay the true stress-strain curve for the material. However, a number of practical difficulties plague spherical indentation. Most importantly, the initial onset of plasticity is difficult to detect, because plastic yield nucleates below the surface at the point of maximum shear stress, and material which has plastically yielded is initially constrained by elastic material. Thus, the proportionality discovered by Tabor is only valid at relatively large strains. Furthermore, as the contact area grows, the volume of material being tested also grows. Thus, both the material volume and the strain are changing concurrently. This difficulty is not insurmountable if the test material is homogenous, but if the material is substantially heterogeneous, then the problem of simultaneously changing both the strain and the material being tested is quite intractable. Generally, uncertainty in contact area is also greater for spheres than for other indenter punch geometries.

Instrumented indentation equipment having a cylindrical indenter punch with a flat-ended surface, namely, a flat-ended indenter, has been proposed, and is commonly used for such purposes as measuring the viscoelastic properties of polymers and biological materials.

Moreover, instrumented indentation equipment having flat-ended and spherical indenters each have been used to perform compression tests on very small pillars fabricated by focused ion-beam milling (FIB) or other micro-fabrication techniques. In these tests, the contact surface of the indenter punch is brought into contact with the top of the "micro-pillar", and then compresses the pillar to the yield point and beyond. The analysis of the indentation force and displacement data generated by this kind of test is identical to that of the force-displacement data produced by a macro-scale compression test, and each test on an individual micro-pillar can be used to construct a full stress-strain curve.

The growing popularity of the pillar-compression technique reveals a great deal about the value and challenge of measuring stress-strain curves on microscopic samples. Producing micro-pillars is time-consuming, and requires expensive equipment and highly experienced operators. Therefore, the fact that those skilled in the art choose to conduct instrumented indentation on micro-pillars demonstrates that no adequate alternative instrumented indentation equipment and techniques presently exist.

Thus, an economical and efficient way of determining the entire stress-strain curve of a sample of material on a scale applicable to nanotechnology by means of instrumented indentation remains a highly desirable but elusive goal.

SUMMARY

According to an aspect of the inventive concept, there is provided a support adapted to support a sample of the material, an indenter including a punch having a longitudinal axis and a flat end surface substantially perpendicular to the longitudinal axis, an actuator coupled to the support and/or the indenter and operable to cause displacement of the punch relative to the support in a direction substantially parallel to the longitudinal axis of the punch, a force detector that outputs data representative of an applied force corresponding to mechanical response of the sample as a reaction to being indented by the punch, a displacement detector that outputs data representative of a depth to which the sample is indented by the punch, and a controller operatively connected to the actuator so as to control the displacement of the punch relative to the support and the force applied by the punch to the sample, operatively connected to the force and displacement detectors so as to receive the data produced by the detectors, and configured to construct a stress-strain curve using the data produced by the detectors.

According to another aspect of the inventive concept, there is provided an instrumented indentation apparatus comprising a support adapted to support a sample of the material, an indenter including a punch having a longitudinal axis and a flat end surface substantially perpendicular to the end surface, an actuator coupled to the support and/or the indenter and operable to cause displacement of the punch relative to the support in a direction substantially parallel to the longitudinal axis of the punch, a force detector that outputs data representative of an applied force corresponding to mechanical response of the sample as a reaction to being contacted by the punch, a displacement detector that outputs data representative of a depth to which the sample is indented by the punch, and a controller operatively connected to the actuator so as to control the displacement of the punch relative to the support and the force applied by the punch to the sample, and operatively connected to the force and displacement detectors so as to receive the data produced by the detectors. The controller is configured to execute a loading operation in which the punch is forced into the sample until a target force or depth is achieved, and to execute an unloading operation in which the punch is withdrawn from the sample once the target force or depth has been achieved. The controller is also configured to calculate values of stress σ of the sample according to an equation:

$$\sigma = \zeta \sigma_m$$

wherein $\zeta$ is a scale factor or function, and $\sigma_m$ is the force applied during the loading operation divided by the area of the end surface of the indenter. The controller is also configured to calculate values of strain ε of the sample according to an equation:

$$\varepsilon = \left(\frac{2}{\pi}\right)\frac{h}{a},$$

wherein h is the depth of indentation during the loading operation, and a' is an effective radius of the end surface of the indenter.

According to another aspect of the inventive concept, there is provided an instrumented indentation method comprising supporting a sample of material having a planar surface, performing a loading operation of indenting the surface of the sample with an end surface of a punch that is flat, generating data representative of forces applied to the sample by the punch during the loading operation, generating data representing the depth of the end surface of the punch relative to the surface of the sample during the loading operation, calculating values of stress of the sample according to an equation:

$$\sigma = \zeta \sigma_m$$

wherein $\zeta$ is a scale factor or function, and $\sigma_m$ is a force applied to the sample during the loading operation divided by the area of the end surface of the punch, and calculating values of strain of the sample, from the data generated during the loading of the sample, according to an equation:

$$\varepsilon = \left(\frac{2}{\pi}\right)\frac{h}{a},$$

wherein h is a depth of penetration of the sample during the loading operation, and a' is an effective radius of the end surface of the punch. In the loading operation, the end surface of the punch is brought into contact with the planar surface of the supported sample with the end surface oriented such that it is substantially parallel to the planar surface of the sample, and then the end surface is forced into the sample in a direction that is substantially perpendicular to the end surface of the punch and the planar surface of the sample.

BRIEF DESCRIPTION OF THE DRAWINGS

These and other features, and objects and advantages of the inventive concept will become apparent from the detailed description of preferred embodiments made with reference to the attached drawings.

DETAILED DESCRIPTION OF THE PREFERRED EMBODIMENTS

Various embodiments and examples of embodiments of the inventive concept, and examples of data produced according to the inventive concept, will be described more fully hereinafter with reference to the accompanying drawings.

In the description that follows it will also be understood that when an element is referred to as being "coupled to", "connected to" or "engaged with" another element, it can be directly coupled to, connected to or engaged with the other element or layer or intervening elements may be present. In contrast, when an element is referred to as being "directly on" or "directly connected to" or "directly engaged with" or "contacting" another element or layer, there are no intervening elements or layers present.

Other terminology used herein for the purpose of describing particular examples or embodiments of the inventive concept is to be taken in context. The term "substantially" is used to indicate a level of preciseness within expected tolerances. Similarly, the term "substantially in the shape of a regular polygon" is used to refer to not only an end surface formed to have the shape of practically any regular polygon but also a polygon whose sides and/or corners may be rounded to some extent but whose sides still have substantially equal lengths. Still further, the terms "comprises" or "comprising" when used in this specification specifies the presence of stated features or processes but does not preclude the presence or additional features or processes.

Figure 2:
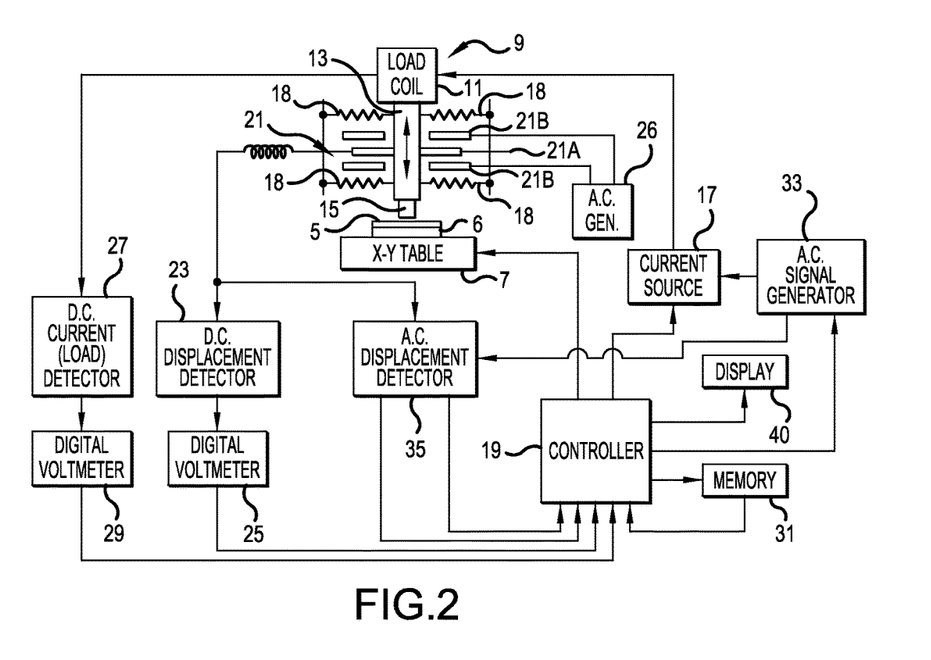
FIG. 2 is a block diagram of an example of instrumented indentation apparatus according to the inventive concept.
Figure 3A:
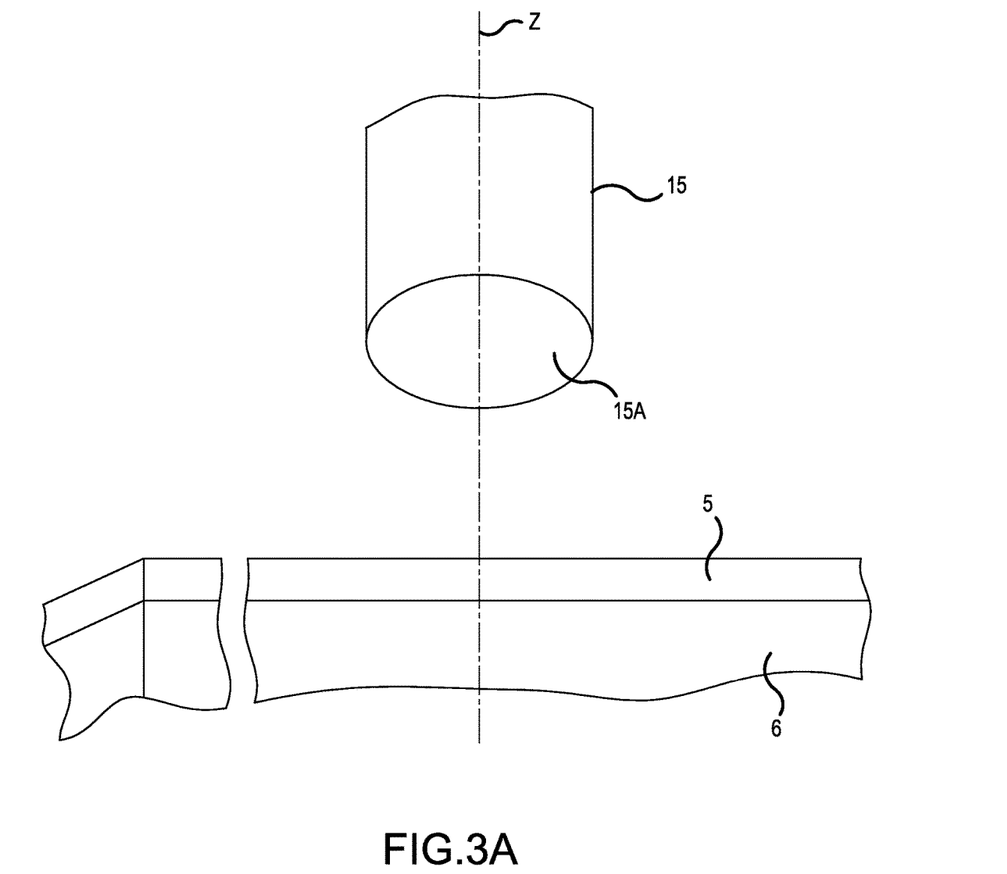
FIG. 3A is a schematic perspective view of part of the apparatus of FIG. 2 including one example of an indenter punch of the apparatus.
Figure 3B:
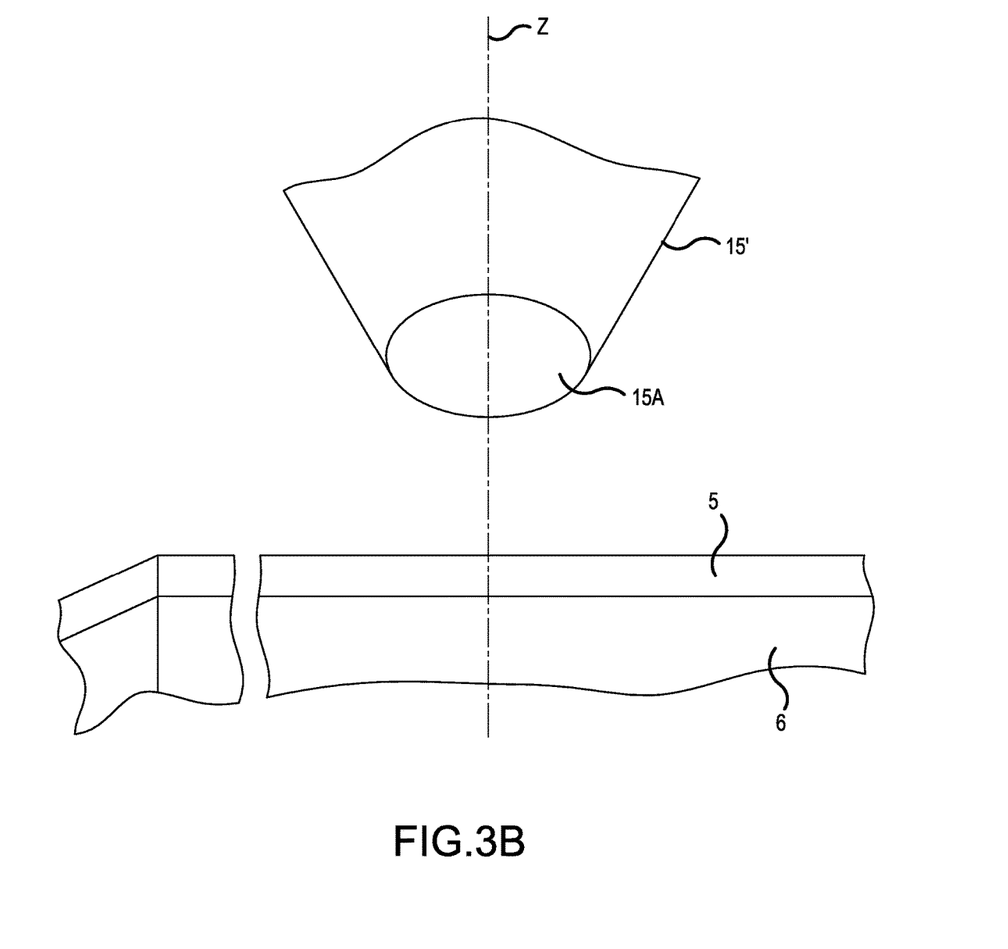
FIG. 3B is a schematic perspective view of part of the apparatus of FIG. 2 including another example of an indenter punch of the apparatus.
Figure 3C:
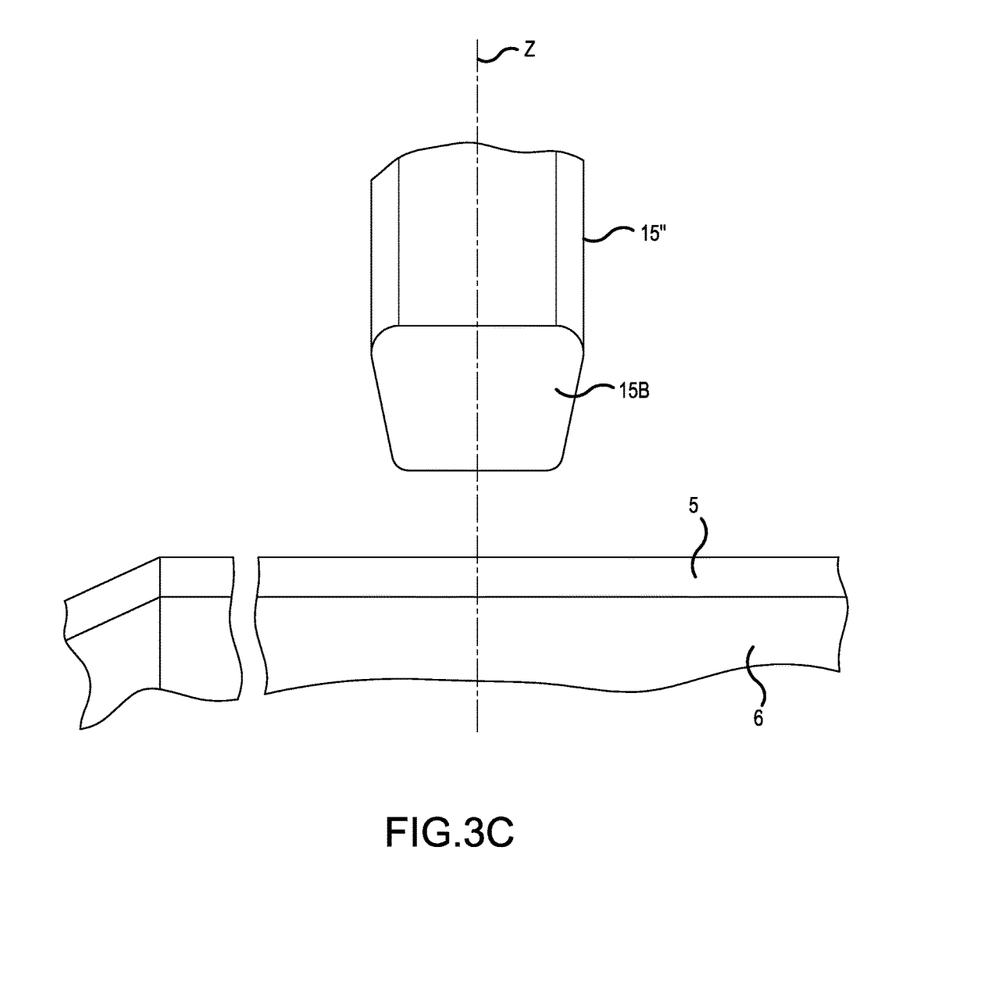
FIG. 3C is a schematic perspective view of part of the apparatus of FIG. 2 including still another example of an indenter punch of the apparatus.

An example of an apparatus for ascertaining a property of material, according to the inventive concept, will now be described with reference to FIGS. 2 and 3. The apparatus is an exemplary system for obtaining force-displacement data from a sample of the material 5, and calculating values of stress and strain from that data. Thus, a mechanical property or properties of the material, e.g., its hardness and/or yield point, can in turn be determined.

A support 6 is generally used to support the sample 5 across its bottom. In this example, the sample 5 is in the form of a thin plate of material and the support 6 supports the entire bottom surface of the sample 5. Furthermore, the dimensions of the sample 5, i.e., the thickness of the sample, may be on the order of nanometers.

The apparatus may also include a stage 7 to which the support 6 can be mounted or is fixed such that the sample 5 cannot deflect relative to the stage. The stage 7 may constitute an X-Y stage so that the sample 5 can be located in a known position in an X-Y plane. The apparatus also has a system computer 19 which may be operatively connected to the X-Y stage 7 to control the movements of the stage along the X and Y axes.

Also, in this example, the surface of the sample 5 to be engaged faces up. Alternatively, the apparatus could be configured so that the surface to be engaged faces downwardly. In either of these cases, the X-Y plane would be a horizontal plane. As another alternative, the apparatus could be configured so that the surface to be engaged faces to the side. In this case, the X-Y plane would be a vertical plane. That is, for purposes of description, X and Y represent any two axes of a Cartesian coordinate system.

An indenter is juxtaposed with the stage 7 and hence, with a sample 5 supported on the stage 7, along a third axis (Z axis) orthogonal to the X-Y plane. The indenter comprises a rod 13 and an indenter punch 15 integral with the rod 13.

According to an aspect of the inventive concept, the indenter punch 15 is flat-ended meaning that it has a longitudinal axis (coinciding with the Z-axis when in place in the apparatus) and an end surface substantially perpendicular to the longitudinal axis. In the example shown in FIG. 3A, the indenter punch is a flat-ended cylinder and has an end surface 15A (FIG. 3) in the form of a disk whose outer periphery is circular. In the example shown in FIG. 3B, the indenter punch 15' is a flat-ended cone, i.e., has the shape of a frustum. In a working example, the taper is at an angle of 60° and the end surface has a diameter of 20 microns. As still another example, the end surface of the indenter punch may have the shape of a regular polygon (triangle, square, hexagon, etc). In this case, the corners and/or sides may be rounded to some extent. FIG. 3C, for example, shows an indenter punch having an end surface whose outer periphery is substantially the shape of a square.

In any case, the indenter punch 15 is supported such that its longitudinal axis extends substantially in the direction of the Z axis and its flat end surface 15A lies substantially parallel to the planar surface of the sample 5 to be engaged. The indenter punch 15 is displaceable relative to the support 6 along the Z-axis (in the directions shown by the double-headed arrow in FIG. 2) so as to apply a load to the sample 5. For example, the throw of the indenter along the Z-axis is +/−1 millimeter.

As can be appreciated by those skilled in the art, such relative movement can be caused by movement of the indenter punch 15, movement of the support 6, or movement of both the indenter punch 15 and the support 6. An actuator 9 coupled to the support 6 and/or indenter can be provided to cause such relative movement. The actuator 9 may be operative to apply a force to the sample, through the indenter punch 15, which is on the order of milliNewtons (mN). The actuator 9 can be a hydraulic, pneumatic, magnetic and/or electric (e.g. electrostatic, electromagnetic, and/or piezoelectric) actuator. The system computer 19 is operatively connected to the actuator 9 to control the relative movement between the support 6 and the indenter punch 15.

In the illustrated example of this embodiment, the actuator 9 comprises a current driven load coil 11 and a variable current source 17 controlled by computer 19 to supply electrical current to the coil 11. In this way, the rod 13 of the indenter may be controlled to move downward such that the end surface 15A of the indenter punch 15 is brought into direct engagement, i.e., contact, with the sample 5. The actuator 9 may include leaf springs 18 which constrain the rod 13 such that the indenter punch 15 can moves only along the Z axis. Once the flat end surface 15a of the indenter punch 15 contacts the sample a force and/or displacement pattern is exerted on the indenter by varying the current supplied to the load coil 11 according to a program provided by the computer 19. The force and/or displacement pattern includes a loading pattern that forces the indenter punch 15 into the sample 5, and an unloading pattern that subsequently withdraws the indenter punch 15 from the sample 5.

Force-displacement responses are obtained during this loading and unloading of the sample, and the responses are used by the computer 19 to calculate values of stress and strain as will be described in more detail later on. To this end, in the illustrated example of this embodiment, the apparatus includes a displacement detector that detects a depth to which the sample has been penetrated by the indenter punch 15, and a force detector to monitor the force applied to the sample by the indenter punch 15 and thus detect a mechanical response of the sample as a reaction to being indented by the punch. The displacement detector also outputs data representative of the penetration depth to the computer 19 and likewise, the force detector also outputs data representative of the force applied to the sample to the computer 19.

The displacement detector includes a sensor 21 that senses displacement of the rod 13 and hence, of the indenter 15 punch, and outputs signals that are measures of the displacement, and a converter (D.C. displacement detector) 23 that is connected to the sensor 21 and computer 19 and is operative to digitalize signals from the sensor 21 and issue the signals to the computer 19. The apparatus may also include a digital voltmeter 25 to which the digital signals from the converter 23 are fed to the computer 19. In this case, the voltmeter 25 provides a calibrated readout of the displacement of the indenter punch 15 to an operator during testing procedures.

Also, in this example, sensor 21 is a capacitive displacement gage known in the art, per se, and includes a center plate 21A which is typically connected to an AC source 26. The center plate 21A is coupled to the rod 13 to move therewith. The drive plates 21B have apertures through which rod 13 extends freely and thus, center plate 21A moves relative to drive plates 21B. The capacitance between the center plate 21A and drive plates 21B is indicative of the relative position of rod 13 and hence, of the displacement of the indenter punch 15, relative to the sample 5. Also, note, the springs 18 in this example are shown separate from the center plate 21A as directly connected to the rod 13; however, springs 18 can also, or in the alternative, be connected directly to the center plate 21A.

Furthermore, as can be appreciated by those skilled in the art, a capacitive displacement gage is but one example of the displacement sensor 21 which may be employed by apparatus according to the inventive concept. For example, the sensor 21 may be of a type based on electromagnetic radiation such as laser interferometers, fiber optic based sensors or radar, magnetically based or other forms of electric based sensors such as strain gages. In addition, any form of sensor used in or suitable for an atomic force microscope could be used.

The force detector, in this embodiment, comprises a DC current detector 27 operatively connected to the load coil 11 to sense the DC drive current flowing through the load coil 11. The detector 27 is operative to digitalize the DC drive current and output the digital signals to the computer 19. The apparatus may include a second digital voltmeter 29 through which the signals are fed to the computer 19 and which provides a calibrated readout to an operator of the force of the indenter punch 15 exerted on the sample during testing procedures.

The apparatus may also have a memory 31 in which data, and system operating parameters and/or programs, are stored. The memory 31 may be a unit separate from the computer 19 or may be an integral component of the computer 19 along with a processor of the computer. In any case, the computer 19 with integrated or separate memory 31 may constitute a controller of the apparatus. The configuration of the computer 19 will be described in more detail below.

Figure 4:
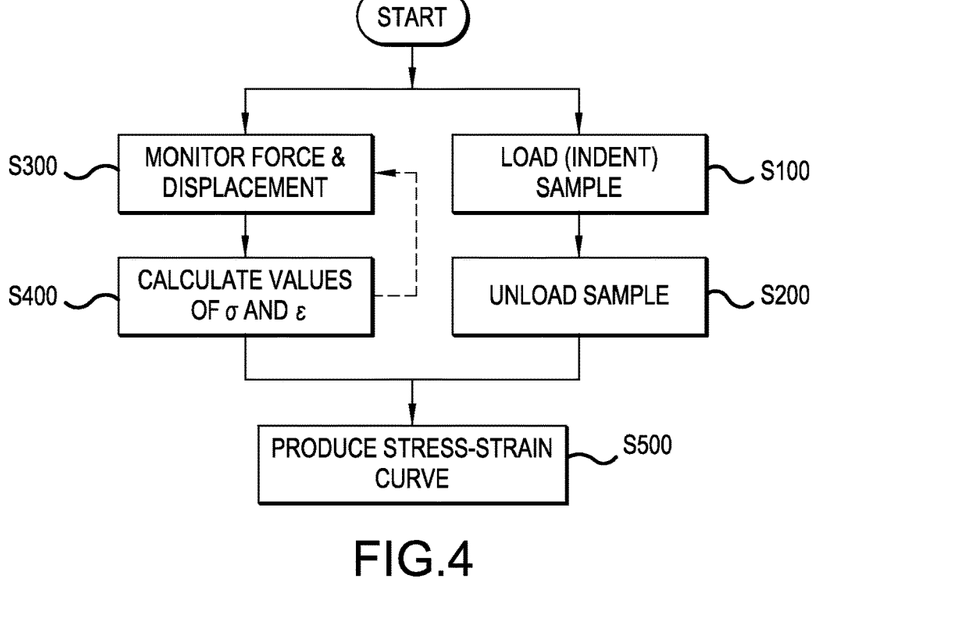
FIG. 4 is a flowchart of an instrumented indentation method of testing a sample according to the inventive concept.

Using the system as described above, a sample 5 of test material mounted to support 6 is positioned at a known location via the X-Y table 7 and the computer 19 is signaled to start the test procedure (refer also to FIG. 4). In response, the indenter punch 15 and the sample are brought together, e.g., the indenter punch 15 is lowered, at a slow rate until the flat end surface 15A of the indenter punch 15 contacts the surface of the sample 5. At this time, the surface of the portion 5A of the sample 5 to be directly engaged is substantially parallel to the end surface 15A of the indenter punch 15.

Then the computer 19 executes the loading pattern part of the aforementioned loading/unloading program (S100). For example, the computer 19 controls the current source 17 to supply an increasing DC current to the load coil 11 of the actuator 9 such that the actuator 9 forces the flat end surface 15A of the indenter punch 15 further towards and into the sample 5 (along the direction of the Z axis) until a predetermined (target) force or displacement is reached. The force or displacement can be static or vary over time either increasing or decreasing such as according to a selected ramping function.

Then the computer 19 executes the unloading pattern part of the aforementioned loading/unloading program (S200). As a result, the indenter punch 15 is withdrawn from the sample with the same or similar pattern of force or displacement.

During at least the loading and unloading steps (S100 and S200), the computer 19 monitors the force applied by the indenter as measured by the DC current detector 27 and the displacement of the indenter punch 15 as measured by the DC displacement detector 23 (S300). Other dynamic channels may also be recorded simultaneously. Respective values of this data may be stored in the memory 31.

Also, during this time (S100 and S200), a small oscillation may be applied by an AC signal to the current source 17 as disclosed in U.S. Pat. No. 7,441,465. Specifically, the apparatus includes means for applying a small mechanical vibrational force to the sample 5 and for monitoring the resulting displacement relative to the applied force (as part of S300). The force may be applied in the form of an oscillatory force (AC force), typically about 10E-8 N (Newtons), by superimposing an AC current onto the DC drive current applied to the load coil 11. The frequency of the AC force applied is preferably in the range of from about 0.5 Hz to 1 MHz and more preferably in the range of from 0.5 to 200 Hz. The amplitude of the oscillating force may be in the range of from about 10E-10 to 1 N, depending on the area of the end surface of the indenter punch, i.e., the area of contact.

To these ends, the apparatus may include an AC signal generator 33 under control of the computer 19 to introduce an AC signal into the output current signal of the current source 17 and an AC displacement detector 35 for detecting the resulting AC displacement. The AC displacement detector 35 may be a lock-in amplifier which is tuned to measure the amplitude of the AC displacement at the applied frequency together with the phase of the displacement signal relative to the applied signal. The amplitude and phase signals are digitalized by the detector 35 and fed to separate inputs of the computer 19 for analysis or storage (in memory 31) along with the DC force and displacement information during the loading and unloading pattern parts of the process program. The force-displacement response data can be provided as an output for use in ascertaining one or more mechanical properties of the material that the sample 5 is made from. Alternatively, computer 19 can perform the necessary calculations using the data and provide the one or more mechanical properties as an output.

In any case, the computer 19 is configured to calculate values of stress ε and strain σ (S400) from points of data of the force and displacement. A stress-strain curve is then produced (constructed) using the force-displacement data (S500). The apparatus may include a display 40 that displays the stress-strain curve. The stress-strain curve may be used to determine at least one mechanical property of sample 5 such as the yield point, hardness, etc.

The values of stress ε and strain σ are calculated (S400) by the computer 19 as follows.

The strain, ε, is calculated for each data point generated during the loading of the sample. e.g., for each point in the loading curve, as:

$$\varepsilon = \left(\frac{2}{\pi}\right)\frac{h}{a},$$

wherein h is the indentation depth, and a' is an effective radius of the end surface of the indenter punch. In the case in which the end surface (15A) is circular, a' is simply the radius (a) of the end surface. In the case in which the end surface has substantially the shape of a polygon, e.g., in which the end surface (15B) has substantially the shape of a square, a'=sqrt(A/π), wherein A is the area of the end surface. In any case, the value of the effective radius a' is a known fixed value that may be stored in the memory 31 of the apparatus. In this embodiment, the effective radius a' is on the order of several microns, and in the examples of FIGS. 3A and 3B is preferably about 10 microns. For purposes of ease of description, reference will be made hereinafter to the example of FIG. 3A The stress σ is calculated for each data point generated during the loading of the sample, e.g., for each point in the loading curve, as:

$$\sigma = \zeta \sigma_m$$

wherein ζ is a scale (described in more detail below), and $\sigma_m$ (the mean contact pressure) is the applied force divided by the area of the end surface 15A of the indenter punch 15 (also known as the indentation hardness). The area of the end surface 15A of the indenter punch 15 is also a fixed value that can be readily calculated from an operator input and/or stored in the memory 31 of the apparatus.

In this embodiment, the scale ζ is a scale function of a stiffness ratio S*, wherein S* is the slope $S_L$ of the loading curve divided by the elastic contact stiffness S. The slope $S_L$ of the loading curve is the slope of the force-penetration curve produced as the indenter punch is penetrating the material of the sample. The elastic contact stiffness S, as is known, can be determined as the slope of the unloading curve (force-penetration curve produced as the indenter punch is first being retracted from the material) or, if a small oscillation is applied, then the amplitude of the force oscillation divided by the amplitude of the displacement oscillation. Examples of valid relationships between ζ and S*, i.e., examples of ζ=f(S*), will be given below.

Generally, the production of the stress-strain curve by instrumented indentation can be divided into two parts: (1) deriving a definition of indentation strain, $\varepsilon_i$, which logically relates to uniaxial strain and (2) deriving a scale, ζ, factor or function which, when multiplied by the mean contact pressure, $\sigma_m$, gives the stress that would be measured during a uniaxial tension or compression test at the strain defined by part (1) of the problem.

Indentation Strain $\varepsilon_i$

For elastic contact between any axisymmetric indenter punch and a test surface, the elastic contact stiffness, S, and an effective radius, a', of the contact surface are related as:

$$S = 2E_r a' \quad (1)$$

wherein $E_r$ is the reduced Young's modulus which incorporates elasticity in both the indenter punch and the sample. It is related to the elastic properties of the test material and the indenter through the relation:

$$\frac{1}{E_r} = \frac{1-v^2}{E} + \frac{1-v_i^2}{v_i} \quad (2)$$

wherein E is the Young's modulus of the test material, v is the Poisson's ratio, and the subscript "i" identifies the corresponding properties of the indenter.

Because the contact radius is constant for indentation using the flat-ended indenter, the elastic contact stiffness is constant and identical to the measured force, P, divided by the measured displacement, h, so long as the contact is elastic. Thus, Eq. 1 can be rewritten as:

$$P/h = 2E_r a' \quad (3)$$

Multiplying both sides of Eq. 3 by the quantity $h/(\pi a'^2)$ gives $$\frac{P}{\pi a'^2} = \sigma_m = \frac{2}{\pi} E_r \frac{h}{a'} \quad (4)$$

If the strain caused by the indentation using the flat-ended indenter is defined as:

$$\varepsilon_i \equiv \left(\frac{2}{\pi}\right) \frac{h}{a'} \quad (5)$$

then the mean contact pressure is linearly related to the indentation strain through the reduced modulus:

$$\sigma_m = E_r \varepsilon_i$$

and the form is analogous to that used to comprehend the elastic part of a uniaxial tension or compression test. Thus, the values of strain will be calculated according to Eq. 5.

Scale Function for Mean Indentation Pressure

The function of ζ should relate the mean contact pressure $\sigma_m$ to the stress σ; which would be measured during a uniaxial tensile test at a strain value which is equivalent to $\varepsilon_i$. That is, an easily known set of values are sought which when multiplied by the mean indentation pressure (contact hardness) give values of stress which, when plotted against strain as defined in Eq. 5, produce a stress-strain curve, $\sigma_i = f(\varepsilon_i)$ which is equivalent to the uniaxial stress-strain curve σ=f(ε) for the material.

The function of ζ relates the indentation stress to the mean contact pressure as:

$$\sigma_i = \zeta \sigma_m \quad (7)$$

Approximate values of ζ throughout the limits of full elasticity and full plasticity are known. Throughout the limit of pure elasticity, the values of ζ should be unity because that is the coefficient of $\sigma_m$ in Eq. 6. Throughout the limit of fully developed plasticity, indentation theory, finite-element analysis, and experiments all indicate that ζ should have a value of about ⅓. Thus, a function, ζ(X) which transitions from unity to ⅓ as the contact transitions from fully elastic to fully plastic, and such that the degree of plasticity is quantified by parameter, X, has been determined according to an aspect of the inventive concept.

That is, as mentioned above, X=S*=$S_L$/S. This stiffness ratio has a number of advantages which make it ideal for quantifying the degree of plasticity.

The stiffness ratio S* is a direct indication of the degree of plasticity induced by the contact. When the contact is fully elastic, S* has a value of unity, because the loading and unloading curves coincide. The theoretical lower bound for S* is zero; S* takes this value if the unloading curve is vertical (no elastic recovery), making the slope of the unloading curve infinite. Thus, the domain for S* is zero (fully plastic) to unity (fully elastic). It is important to note that S* can be determined continuously and for each recorded data point in the loading curve.

Thus, function ζ=f(S*) should return values of ζ that can be multiplied by the mean contact pressure, $\sigma_m$ (hardness), to obtain the stresses which correspond to the strains as defined in Eq. 5. In order to determine the precise form of function, f(S*), finite-element simulations of indentations according to the inventive concept, i.e., using a cylindrical flat-ended indenter punch, into materials with known stress-strain curves (which are simulation inputs) were conducted.

Values of the indentation strain were calculated according to Eq. 5 from the results of these simulated indentations. Then, values of the true stress, σ, were calculated for each value of $\varepsilon_i$ as using the input stress-strain relations. Finally, the values of ζ were calculated dividing σ by the mean contact pressure, $\sigma_m$, and ζ was related to the ratio S* as shown in FIG. 5A.

Figure 5A:
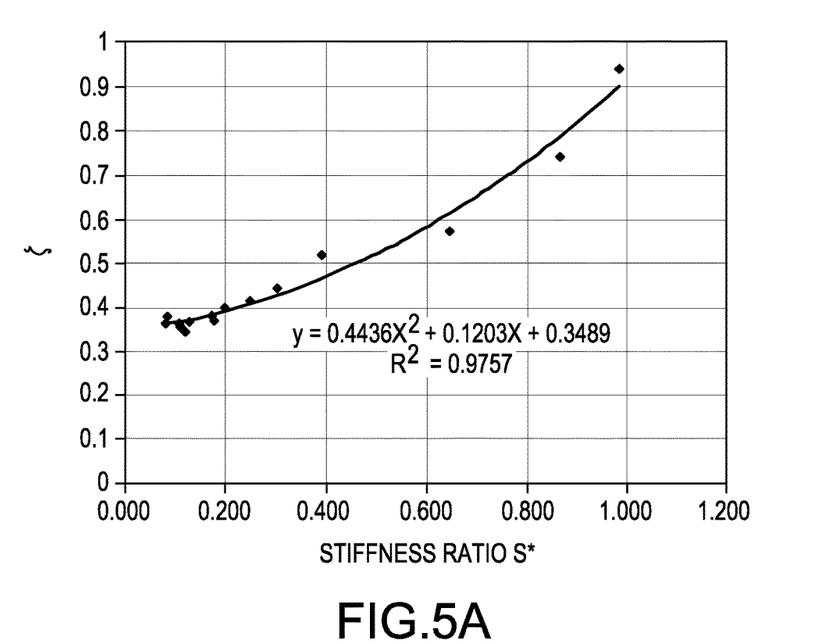
FIG. 5A is a graph of a best fit curve representing an example of a scaling function for use in calculating values of stress from force-displacement data according to the inventive concept.
Figure 5B:
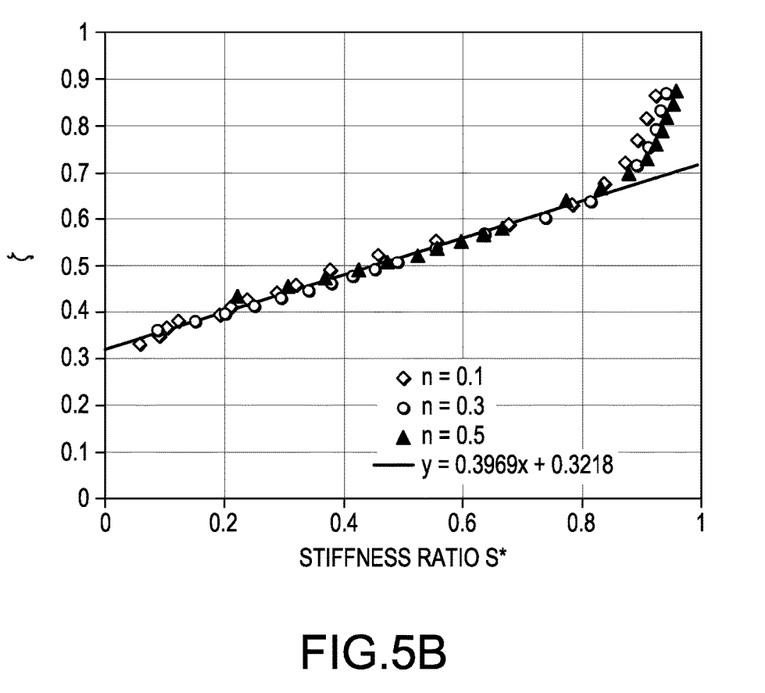
FIG. 5B is a graph of a best fit curve representing another example of a scaling function for use in calculating values of stress from force-displacement data according to the inventive concept.

It is submitted that the relation shown in FIG. 5A is generally true for all indentation processes using a flat-ended indenter punch, virtual and experimental, although the precise form of or the values of constants for the best fit curve may be improved by incorporating the results from additional simulations. For example, the inventor has carried out additional simulations which yielded an improved function, ζ=f(S*), shown in FIG. 5B.

Further in this respect, the inventor has conducted finite-element simulations of indentation processes based on other contact geometries and these have shown that the relationship between mean contact pressure and yield stress depends slightly on the degree of friction between the indenter punch and the sample. However, there is reason to suspect an even smaller dependence on friction when using a flat-ended indenter punch because the force resolved along the cylindrical interface is theoretically zero.

In any case, it should also be noted that the scaling function, ζ=f(S*), behaves as expected in the limits of full elasticity and full plasticity. As S* approaches unity, indicating dominant elasticity, ζ approaches unity as we expect from Eq. 6. As S* approaches zero, indicating dominant plasticity, ζ approaches about ⅓ as expected. Moreover, the value of the shift in the best-fit equation is 0.3489 in the case of FIG. 5A and 0.3218 in the case of FIG. 5B, both of which are very close to the value of the scaling factor of 0.357 provided by Tabor to describe spherical indentations at large strains.

Next, the validity of the analysis of the force-displacement data in the case of FIG. 5A according to the inventive concept was confirmed, as follows.

Figure 6:
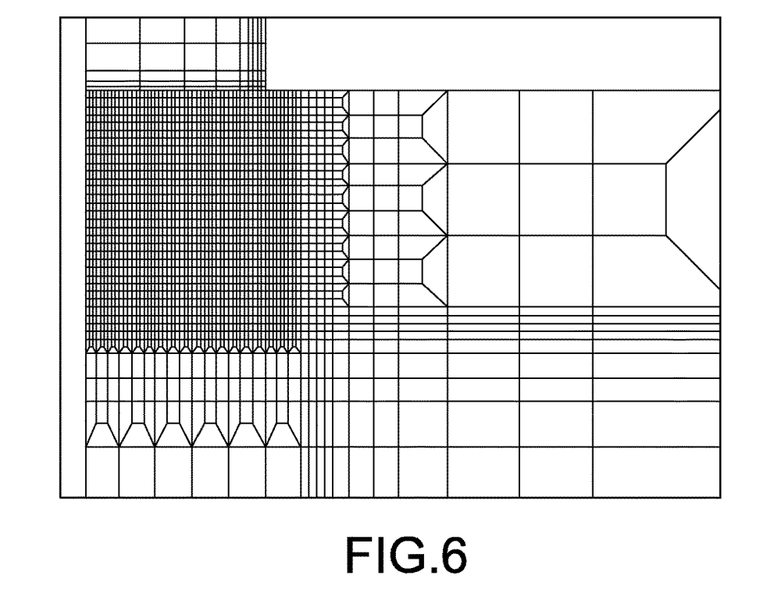
FIG. 6 is a diagram of a mesh generated in a finite element analysis of results of a simulation of an instrumented indentation method according to the inventive concept.
Figure 7:
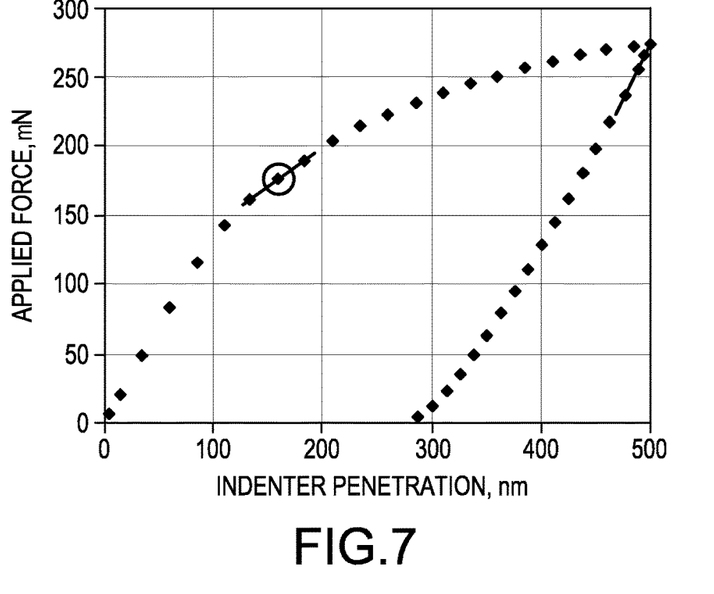
FIG. 7 is an example of a loading-unloading curve of the simulation.

The process of constructing the stress-strain curve for a material from data generated by indenting the material was demonstrated using a finite-element simulation of indenting Aluminum 6061-T6. It should be noted that this was not one of the virtual materials used to determine the function ζ=f(S*) in FIG. 5A. The true stress-strain curve for Al 6061-T6 was determined by uniaxial tensile testing, and used as input to the simulation. In the simulation, the indenter punch had a radius of 10 μm pressed 0.5 μm into the surface of the metal. FIG. 6 shows the mesh at the beginning of the simulation, and the fundamental "measurements" are plotted in FIG. 7. The objective was to produce the stress-strain curve from the data in FIG. 7 and compare that curve to the true stress-strain curve which was used as input to the simulation.

The indentation strain for each displacement value, h, during loading was calculated as:

$$\varepsilon_i \equiv \left(\frac{2}{\pi}\right) \frac{h}{10 \text{ μm}} \quad (9)$$

To get the indentation stress, first, the mean contact pressure was calculating from each force value, P, during loading as:

$$\sigma_m = \frac{P}{\pi (10 \text{ μm})^2} \quad (10)$$

For each point in the loading curve, $S_L$ was calculated as the slope of the curve between the immediate point and the prior point as:

$$S_L = \frac{P_j - P_{j-1}}{h_j - h_{j-1}} \quad (11)$$

and the contact stiffness, S, was calculated from the slope of the unloading curve in the known manner. The stiffness ratio is calculated as:

$$S^* = S_L/S \quad (12)$$

With each value of S*, ζ was calculated for each point in the loading curve from the function derived from the best fit curve in FIG. 5, as $$\zeta = 0.4436(S^*)^2 + 0.1203(S^*) + 0.3489 \quad (13)$$

Finally, the stress for each point in the loading curve was calculated as:

$$\sigma_i = \zeta \sigma_m \quad (14)$$

Figure 8:
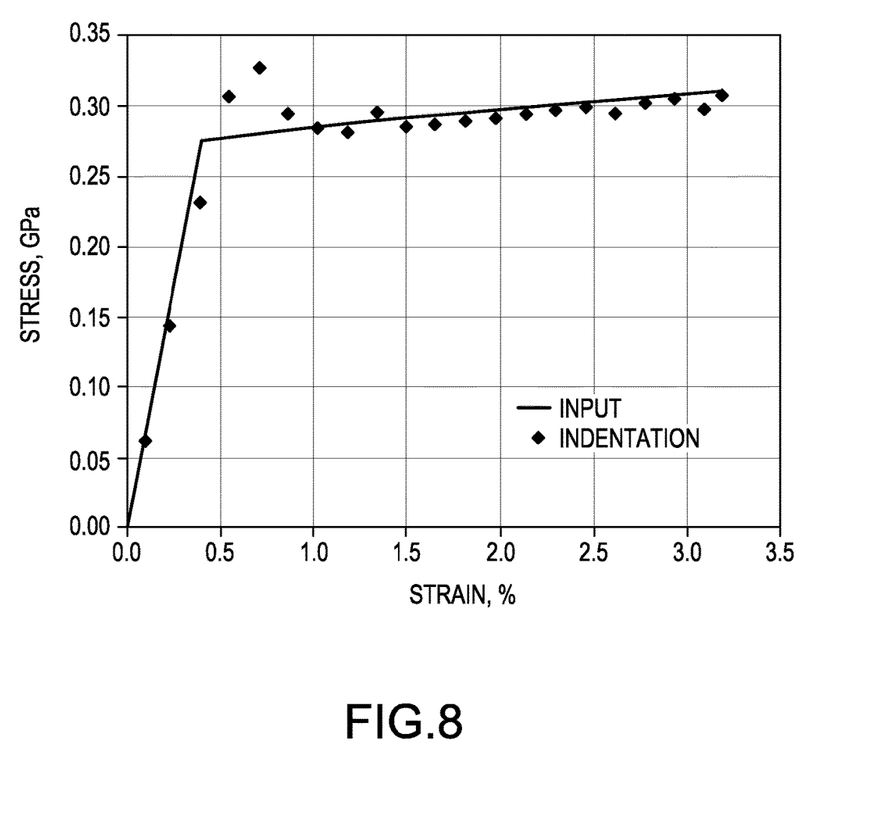
FIG. 8 is a graph of an example of data points of stress vs. strain during loading and unloading in the simulation according to the inventive concept as shown against a stress-strain curve constructed from force-displacement data obtained in a macro scale tensile test conducted on a corresponding sample of material.

FIG. 8 compares the stress-strain curve from the simulated indentation test produced from the calculations of Eqs. 9-14 with the input true stress-strain curve. As can be seen from the figure, the comparison is quite good, which verifies the indentation test according to the inventive concept. However, as one caveat, one of the practical difficulties of the test is that parallelism between the end surface 15A of the indenter punch and the flat surface of the sample 5 to be engaged is never perfect. Thus, the initial part of the loading curve might not be useful for determining the Young's modulus of the material of the sample. Regardless, the Young's modulus is commonly determined from the unloading curve anyway. The initial part of the stress-strain curve may be produced (S500 in FIG. 4) using the Young's modulus determined from unloading, and the calculations based on Eqs. 9-14 can be used to construct the remainder of the stress strain-curve only once full contact has been established between surface 15A and the surface of the sample 5 to be engaged as evidenced by the achievement of a stable stiffness.

According to an aspect of the inventive concept as described above, a flat-ended indenter punch is provided so as to impose a changing strain on a sample of test material, thus allowing a precise relationship between stress and strain to be derived. In contrast with spherical indenters, the maximum shear stress in the test material occurs at the surface (at the edge of contact) and so the onset of plastic yield is more easily detected. The effective contact radius, a', is both known and constant throughout the test; it is simply the contact radius of the end surface of the indenter punch. Furthermore, the volume of material affected by indentation remains approximately constant because the contact radius is constant, which means that the strain can be increased without incorporating new material into the test. And, unlike micropillar compression, the inventive concept does not require any special sample preparation, i.e., any preparation beyond that which is conventionally carried out in instrumented indentation.

Finally, embodiments of the inventive concept and examples thereof have been described above in detail. The inventive concept may, however, be embodied in many different forms and should not be construed as being limited to the embodiments described above. Rather, these embodiments were described so that this disclosure is thorough and complete, and fully conveys the inventive concept to those skilled in the art. Thus, the true spirit and scope of the inventive concept is not limited by the embodiment and examples described above but by the following claims.

What is claimed is:

1. An instrumented indentation apparatus comprising:
a support adapted to support a sample of a material;
an indenter including a punch having a longitudinal axis and a flat end surface substantially perpendicular to the longitudinal axis, wherein an end of the indenter has a shape of a frustum;
an actuator coupled to the support and/or the indenter and operable to cause displacement of the punch relative to the support in a direction substantially parallel to the longitudinal axis of the punch;
a force detector that outputs data representative of an applied force corresponding to mechanical response of the sample as a reaction to being contacted by the punch;
a displacement detector that outputs data representative of a depth to which the sample is indented by the punch; and
a controller operatively connected to the actuator so as to control the displacement of the punch relative to the support and the force applied by the punch to the sample, and operatively connected to the force and displacement detectors so as to receive the data produced by the force and displacement detectors, and
wherein the controller is configured to execute a loading operation in which the punch is forced into the sample until a target force or depth is achieved,
the controller is configured to execute an unloading operation in which the punch is withdrawn from the sample once the target force or depth has been achieved,
the controller is configured to calculate values of stress $\sigma$ of the sample according to an equation:

$$\sigma = \zeta \sigma_m$$

wherein $\zeta$ is a scale function of a stiffness ratio that is a slope of a loading curve divided by an elastic contact stiffness of the sample, and $\sigma_m$ is the force applied during the loading operation divided by an area of the end surface of the punch, and
the controller is configured to calculate values of strain $\varepsilon$ of the sample according to an equation:

$$\varepsilon = \left(\frac{2}{\pi}\right)\frac{h}{a'}$$

where h is the depth of indentation during the loading operation, and a' is an effective radius of the end surface of the punch, wherein the controller is configured to construct a stress-strain curve using the data produced by the force and displacement detectors.

2. The apparatus as claimed in claim 1, wherein the controller is configured to construct a stress-strain curve using respective values of the stress and strain.

3. The apparatus as claimed in claim 2, further comprising a display, and wherein the controller is operatively connected to the display such that the stress-strain curve can be displayed by the apparatus.

4. The apparatus as claimed in claim 2, wherein the controller is configured to construct an unloading curve of the data, detected during the unloading operation, of the force applied to the sample by the punch versus the depth of penetration of the punch in the sample,
the controller is configured to calculate the Young's modulus of the material from the data generated during the unloading operation, and
the controller is configured to use the Young's modulus to construct an initial part of the stress-strain curve.

5. The apparatus as claimed in claim 1, further comprising a memory in which a function of $\zeta$ is stored, and wherein the controller is configured to calculate values of $\zeta$ based on the function.

6. The apparatus as claimed in claim 5, wherein the controller is configured to construct, from the data detected during the loading operation, the loading curve of the force applied to the sample by the punch versus the depth of penetration of the punch in the sample, wherein the slope of the loading curve is a slope of a force-penetration curve produced as the indenter penetrates the sample.

7. The apparatus as claimed in claim 1, wherein the actuator is operative to exert force on the order of milliNewtons (mN).

8. The apparatus as claimed in claim 1, wherein the effective radius of the end surface is on the order of several microns.

9. The apparatus as claimed in claim 1, wherein the outer periphery of the end surface of the punch is circular.

10. The apparatus as claimed in claim 1, wherein the stress-strain curve is an entire stress-strain curve of the sample.

11. The apparatus of claim 1, wherein the force exerted on the sample by the punch during the loading operation is on the order of milliNewtons (mN).

12. The apparatus of claim 1, wherein the sample has a thickness on the order of nanometers.

* * * * *